(12) United States Patent
Ross

(10) Patent No.: US 7,780,612 B2
(45) Date of Patent: Aug. 24, 2010

(54) ADJUSTABLE TISSUE COMPRESSION DEVICE

(76) Inventor: Bradley Allan Ross, Box 619 (27 Nora Street), Stony Mountain, Manitoba R0C 3A0 (CA)

( * ) Notice: Subject to any disclaimer, the term of this patent is extended or adjusted under 35 U.S.C. 154(b) by 278 days.

(21) Appl. No.: 11/702,123

(22) Filed: Feb. 5, 2007

(65) Prior Publication Data

US 2007/0239092 A1 Oct. 11, 2007

Related U.S. Application Data

(63) Continuation-in-part of application No. PCT/CA2005/001211, filed on Aug. 4, 2005.

(60) Provisional application No. 60/598,431, filed on Aug. 4, 2004, provisional application No. 60/635,609, filed on Dec. 14, 2004.

(51) Int. Cl.
*A61F 5/00* (2006.01)
*A61F 5/28* (2006.01)
*A61F 5/24* (2006.01)
*A61B 17/00* (2006.01)

(52) U.S. Cl. ............ 602/5; 128/99.1; 128/121.1; 602/36; 602/21; 606/201; 606/204

(58) Field of Classification Search .......... 602/5, 602/20, 21, 36, 38, 40; 606/201, 204; 16/414; 128/99.1, 121.1, 878, 887

See application file for complete search history.

(56) References Cited

U.S. PATENT DOCUMENTS

| | | | | | |
|---|---|---|---|---|---|
| 1,281,653 | A | * | 10/1918 | Plummer | 606/203 |
| 2,703,725 | A | * | 3/1955 | Vagi | 292/70 |
| 4,479,495 | A | * | 10/1984 | Isaacson | 606/204 |
| 4,583,555 | A | * | 4/1986 | Malcom et al. | 600/595 |
| 5,078,728 | A | * | 1/1992 | Giarratano | 606/204 |
| 5,094,227 | A | * | 3/1992 | Eglauf et al. | 601/135 |
| 5,154,690 | A | * | 10/1992 | Shiono | 602/5 |
| 5,584,854 | A | * | 12/1996 | Minarik | 606/201 |
| 5,642,739 | A | * | 7/1997 | Fareed | 128/881 |
| 5,695,520 | A | * | 12/1997 | Bruckner et al. | 606/204 |
| 5,709,647 | A | * | 1/1998 | Ferber | 601/134 |
| 5,863,782 | A | * | 1/1999 | Hopwood et al. | 435/195 |
| 6,077,242 | A | * | 6/2000 | Falk et al. | 602/62 |
| 6,497,673 | B2 | * | 12/2002 | Rogalski | 602/20 |
| 6,863,657 | B1 | * | 3/2005 | Clements et al. | 602/26 |

* cited by examiner

*Primary Examiner*—Patricia M Bianco
*Assistant Examiner*—Victoria Hicks
(74) *Attorney, Agent, or Firm*—Michael R. Williams; Ade & Company

(57) ABSTRACT

A medical device is arranged to provide adjustable, user-controlled, perpendicular compression to soft tissues. In a preferred embodiment, the pressure is adjusted by a threaded bolt or threaded bolt assembly incorporated into the design of a threaded mounting plate.

13 Claims, 10 Drawing Sheets

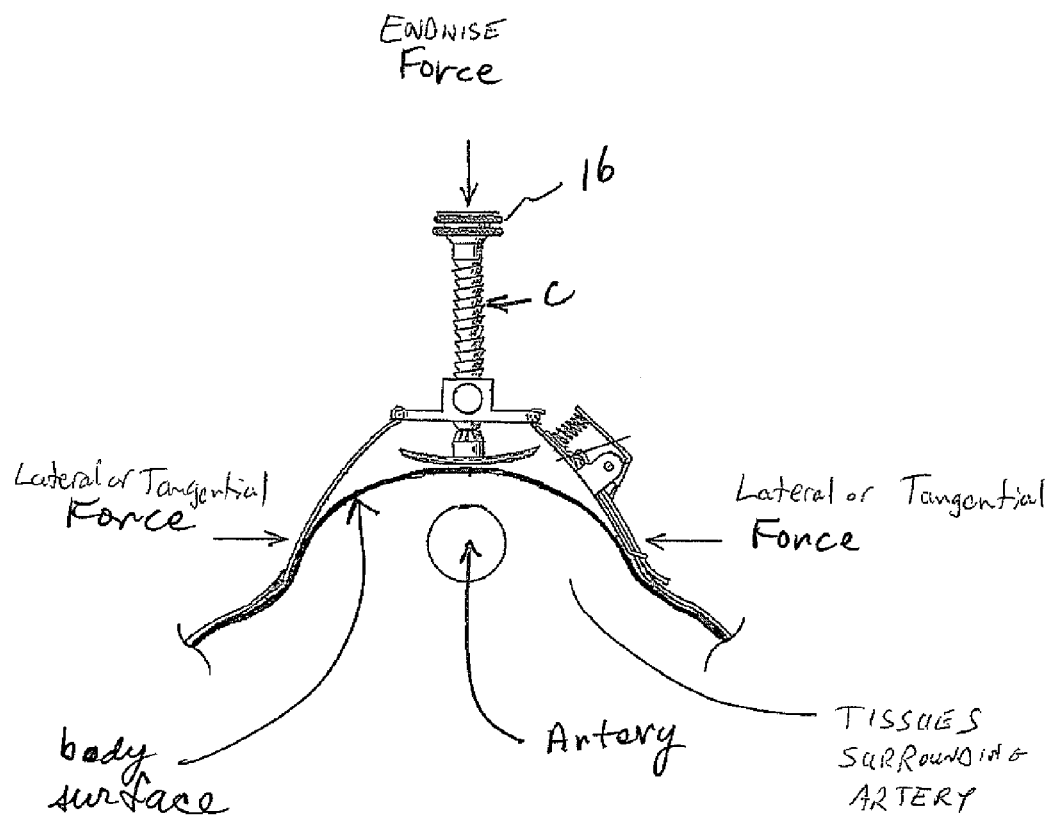

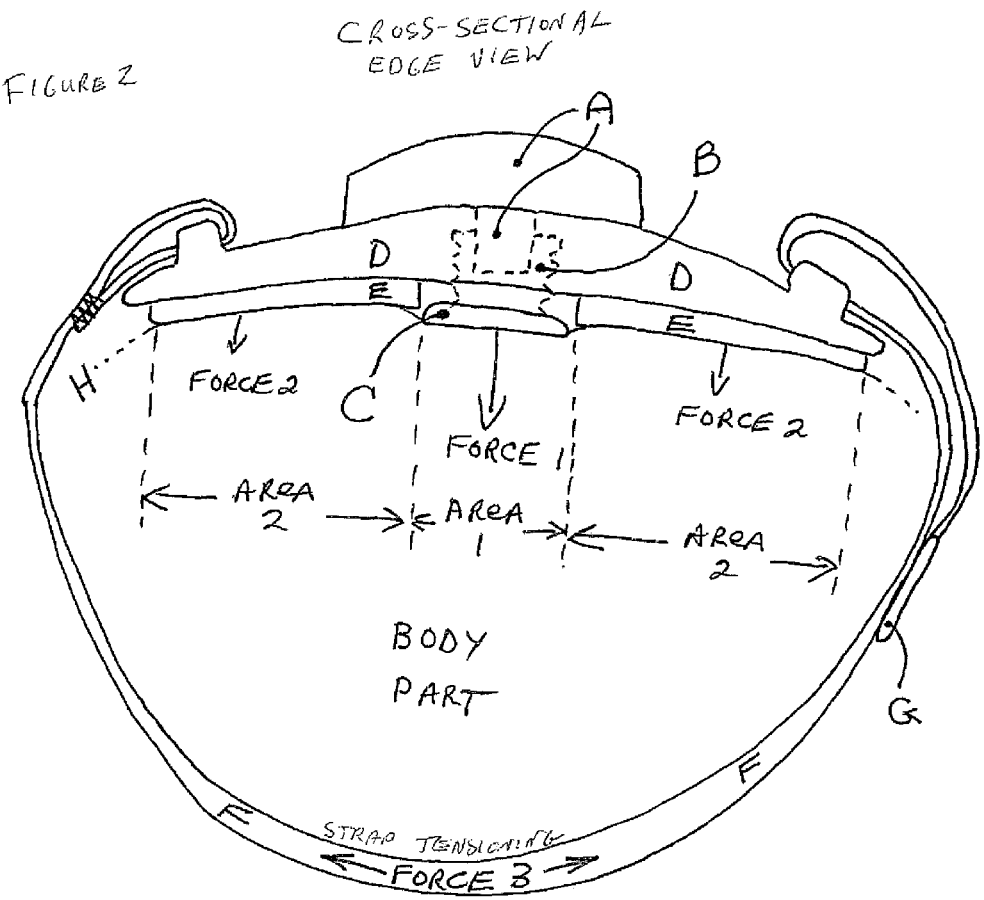
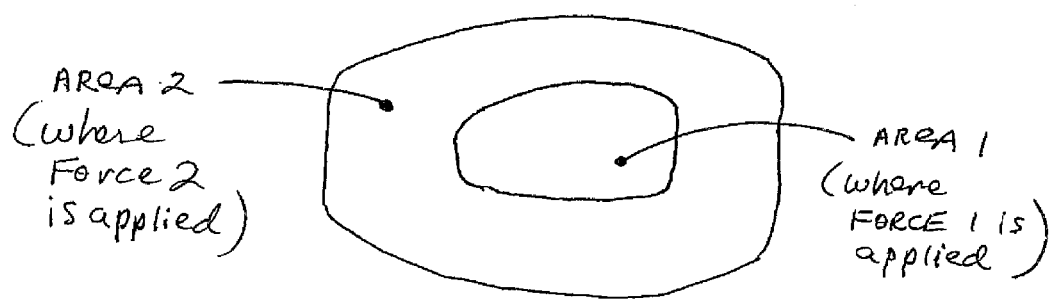

ADJUSTABLE TISSUE COMPRESSION DEVICE

PRIOR APPLICATION INFORMATION

This application is a continuation-in-part of International Application PCT CA2005/001211, filed internationally on Aug. 4, 2005, which in turn claims the benefit of U.S. Provisional Application 60/598,431, filed Aug. 4, 2004 and of U.S. Provisional Application 60/635,609, filed Dec. 14, 2004.

BACKGROUND OF THE INVENTION

Existing medical devices utilize non-boney or non-spinal i.e. "soft" tissue compression in the prevention and/or treatment of pain and/or inflammation and/or muscle spasm and/or repetitive tendon strain and/or nausea. Many of these devices apply predominantly general and circumferential compression forces to such soft tissues. In these devices, adjusting the compression force applied to targeted soft tissues requires that an adjustment be made to the mechanism which encircles the body part (i.e. tightening or loosening the device in a circumferential manner). Many of these devices do not allow local perpendicular compression force adjustment to be made separately from and/or in addition to general circumferential compression force adjustment. The preferred method of compression applies more localized and more perpendicular tissue compression forces by means of a threaded bolt assembly or by means of a threaded bolt, whereby either the pressure foot or the articulating surface of the threaded bolt respectively apply localized adjustable perpendicular compression to the targeted soft tissues. In addition, the preferred method of compression applies more generalized tissue compression by means of the articulating surface of a mounting plate(s) whereby the amount of compression is adjusted by making circumferential tension adjustments to a strap or straps. In the preferred method, the threaded bolt assembly or threaded bolt are mounted on the mounting plate. By this arrangement, the amount of compression applied to targeted tissues by the pressure foot or by the articulating surface of the threaded bolt and the amount of compression applied to the surrounding tissues by the mounting plate may differ based upon the user's comfort, clinical symptoms and functional demands.

For example, U.S. Pat. No. 5,152,302 and U.S. Pat. No. 5,295,951 teach a forearm transaxial compression band that is fitted around the forearm to alleviate the symptoms of lateral or medial epicondylitis. The device has opposing inwardly protruding means that direct transaxial compression against the radial extensor, supinator complex and flexor muscles when the band is circumferentially tensioned and fastened in place around the forearm.

U.S. Pat. No. 6,077,241 teaches a forearm transaxial compression band that has two elongate arcuate compression plates adjustably linked end to end by straps which are flexible to wrap around the limb but are made of inelastic material that doesn't stretch length-wise.

Within the three patents listed above, the adjustment of transaxial i.e. perpendicular compression forces being applied to the limb or body part is accomplished solely by means of adjusting circumferentially the tension on the device strapping system. There is no ability to adjust perpendicular compression forces independent of making adjustments to the circumferential tension of the strapping system. Secondly, these patents describe application which appears to be limited to the elbow region.

U.S. Pat. No. 5,441,058 teaches a method for treating carpal tunnel syndrome using an adjustable strap that is circumferentially fitted around the forearm. The strap is a generally band-shaped device having two opposing inwardly protruding structures on its forearm contacting surface.

U.S. Pat. No. 5,470,304 teaches an apparatus and method for providing pressure point therapy comprising a belt that is secured about the waist of a user and includes a panel that is positioned against the lower back region. The main panel includes several apertures corresponding to possible points of therapy. Threaded pins are inserted into the apertures corresponding to a point in the lower back where pain is experienced. It is of note that this device describes several apertures in a single plate corresponding to possible points of therapy on the lower back.

U.S. Pat. No. 5,797,955 teaches a pressure application unit for positioning vertebra. The device has an upper body vest adapted to substantially surround the upper body of a patient and a pressure applicator unit which has a plunger or thrust mechanism such as a screw with a cushion on the end thereof and mounted for controlled, reciprocal movement in a direction toward the spine for applying external pressure in a controlled manner to one or more vertebra areas. Thus, this device is for applying external pressure to one or more vertebra for repositioning the same and/or maintaining the position thereof in the spinal column, or for forcing and maintaining segments of a broken vertebra in healing contact with each other. Furthermore, pressure is applied to a plate.

U.S. Pat. No. 5,709,647 teaches an acupressure device for stimulating an LI-4 acupressure point comprising in some embodiments, a glove having two arms pivotally attached at a fulcrum and a pressure nodule. It is of note that the glove and nodule apparatus is not shaped so as to be suitable for application to body parts other than to the hand.

U.S. Pat. No. 5,078,728 teaches a strap which encircles the distal forearm and includes a pressure bead which is positioned to lie over and to press upon the Neiguan (Pericardium 6 or P6) acupuncture point. The user may increase compression upon the P6 point by reaching over with the other hand and applying pressure to over the bead. Thus, this patent requires that the user apply pressure with their opposite hand in the event that increased acupuncture point compression and stimulation are desired.

U.S. Pat. No. 5,584,854 teaches a number of clamps for applying acupressure for a variety of body parts. One embodiment, for application to the foot or to the leg immediately below the knee comprises a rectangular mounting plate, fastening straps and a screw which extends through the mounting plate and terminates in a small, spherical pressing tip. The pressing tip has a diameter of approximately 0.22 inches. It is also noted that this patent teaches the use of clamps for use on the toes, heel, hands and feet of a user.

U.S. Pat. No. 5,094,227 teaches a mechanical apparatus for applying pressure to the large intestine 4 (LI4) acupuncture point. The apparatus comprises a clamp which is tightened through the action of a ratchet and further includes a screw for "fine-tuning" the amount of pressure applied to the pressure point.

U.S. Pat. No. 4,320,760 teaches the use of two clamping members in order to deliver acupressure stimulation to selected acupuncture points.

SUMMARY OF THE INVENTION

According to a first aspect of the invention, there is provided a medical device comprising:

a mounting plate having a threaded hole extending therethrough; and a threaded bolt inserted into the threaded hole.

According to a second aspect of the invention, there is provided a method of supplying perpendicular compression to a soft tissue comprising:

providing a medical device comprising:

a mounting plate having a threaded hole extending therethrough; and a threaded bolt inserted into the threaded hole;

positioning the device on a body part of an individual in need of such treatment such that the threaded hole lies over a tissue to be compressed; and turning the threaded bolt until the desired compression of the tissue to be compressed is attained.

According to a third aspect of the invention, there is provided a method of treating lateral epicondylitis of the elbow comprising:

providing a medical device comprising:

a mounting plate having a threaded hole extending therethrough;

a threaded bolt inserted into the threaded hole; and turning means operably connected to the threaded bolt;

positioning the threaded bolt over the central core of the mass of the extensor compartment musculature of the forearm of an individual in need of such treatment; and applying compression to the central core of the mass of the extensor compartment musculature via the turning means such that the threaded bolt contacts the central core of the mass of the extensor compartment musculature.

According to a fourth aspect of the invention, there is provided a method of treating medial epicondylitis of the elbow comprising:

providing a medical device comprising:

a mounting plate having a threaded hole extending therethrough;

a threaded bolt inserted into the threaded hole; and turning means operably linked to the threaded bolt positioning the threaded bolt over the central core of the mass of the flexor compartment musculature of the forearm of an individual in need of such treatment; and engaging the turning means such that the threaded bolt compresses the central core of the mass of the extensor compartment musculature.

According to a fifth aspect of the invention, there is provided a method of applying acupressure to the pericardium 6 (P6) pressure point comprising:

providing a medical device comprising:

a mounting plate having a threaded hole extending therethrough;

a threaded bolt inserted into the threaded hole; and turning means;

positioning the threaded bolt over the P6 pressure point in the region of the tendons of the palmaris longus muscle and the flexor carpi radialis muscle of an individual in need of such treatment; and engaging the turning means such that the threaded bolt compresses at and about the P6 pressure point between and about the tendons of the palmaris longus muscle and the flexor carpi radialis muscle.

According to a sixth aspect of the invention, there is provided a method of treating patellar tendonitis comprising:

providing a medical device comprising:

a mounting plate having a threaded hole extending therethrough;

a threaded bolt inserted into the threaded hole; and turning means;

positioning the threaded bolt over the patellar tendon of an individual in need of such treatment; and engaging the turning means such that the threaded bolt compresses the patellar tendon.

According to a seventh aspect of the invention, there is provided a kit comprising:

a plurality of mounting plates;

a plurality of straps;

at least one threaded bolt; and at least one pressure foot arranged to be mounted onto the threaded bolt.

According to an eighth aspect of the invention, there is provided a method of compressing into the floor of the groove overlying the suspensory ligament of a horse comprising:

providing a device having two bars, each bar having two threaded bolts connected thereto, each said threaded bolt being connected to the bar at a position near to a respective end of the bar, each said threaded bolt having turning means operably linked thereto;

positioning the device such that a respective bar is positioned on each side of the suspensory ligament of a horse in need of such treatment; and engaging the turning means of each threaded bolt such that the desired compression is attained along a length of the suspensory ligament.

The invention will now be described in accordance with the drawings.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a medical device arranged to provide adjustable, user-controlled, perpendicular compression to tissues. In a preferred embodiment, the pressure is adjusted by means of a threaded bolt or of a threaded bolt assembly incorporated into the design of a mounting plate, as discussed below. As will be appreciated by one of skill in the art, depending on the context, 'threaded bolt' and 'threaded bolt assembly' may be used interchangeably in some instances. The device may be used for a variety of purposes, for example but by no means limited to the treatment, amelioration, reduction, prevention and/or control of muscle spasm and/or tendon tissue strain and/or tensile tissue stresses and/or repetitive strain and/or pain and/or tissue inflammation and/or peripheral nerve lesions and/or nausea and/or vomiting and/or morning sickness and/or motion sickness and/or local hematoma and/or local edema.

Figure 1:
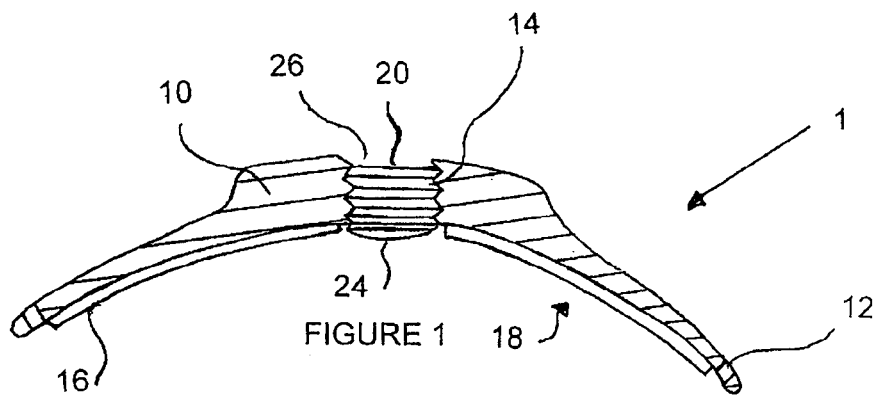
FIG. 1 is a side view of the device in cross section.

Referring to the drawings, the device 1 comprises a mounting plate 10 and a threaded bolt 20, as seen in FIG. 1.

The mounting plate 10 has a flat or substantially concave shape such that the mounting plate 10 is arranged to accommodate or contour to the shape of the body part to which it is applied, as can be seen in FIG. 1. It is of note that the mounting plate 10 may be made of any suitable material, for example but by no means limited to plastic or rubber or other malleable, flexible, semi-rigid or rigid material known in the art. Specifically, the mounting plate 10 is arranged to approximately fit the curvature of the limb of the user or patient. The size, shape and curvature of the mounting plate 10 will depend on the targeted body region but will also depend on the size and shape of the intended user. In some embodiments, the mounting plate 10 is arranged to be sufficiently flexible to be "one size fits all". As will be appreciated by one of skill in the art, the specific curvature of the mounting plate 10 and the size and shape thereof may of course depend on the intended use, as discussed herein. The mounting plate 10 may be sized with one size for all users or patients or one may be of varying sizes based on differences in the sizes of users or patients. The mounting plate 10 includes slots 12 for inserting straps or other connecting means therein, as discussed below and a threaded hole 14 arranged to accept the threaded bolt or threaded bolt assembly 20 therein, as discussed below. In some embodiments, the mounting plate 10 includes padding 16 mounted on the underside or base 18 of the mounting plate 10, that is, such that the surface of the padding 16 contacts the user, as discussed below.

Figure 8:
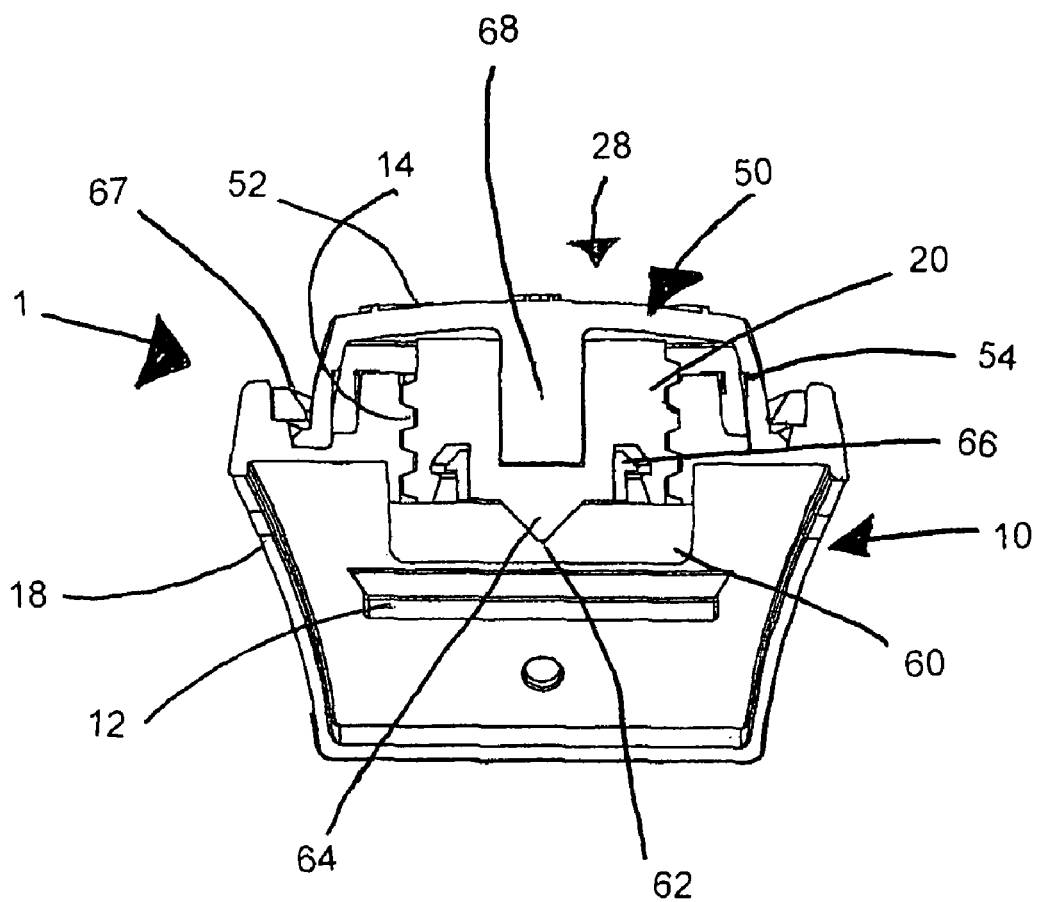
FIG. 8 is a side view in cross-section of one embodiment of the device.
Figure 3:
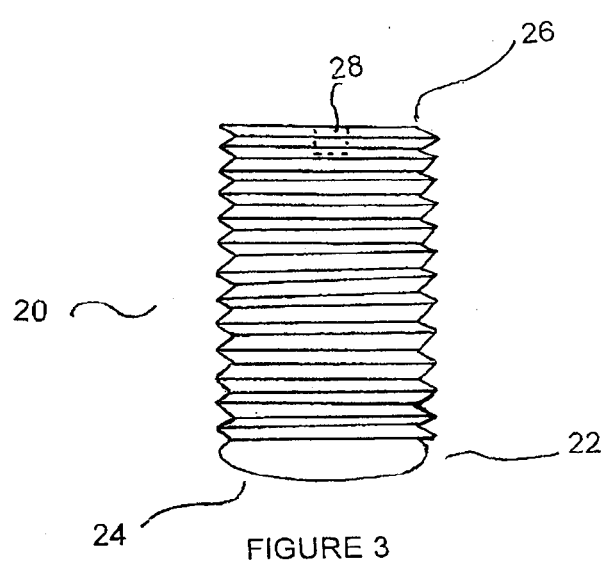
FIG. 3 is a side view of one embodiment of the threaded bolt.

In some embodiments, the threaded bolt 20 has rounded edges 22 and a base 24 as seen in FIG. 3. The base 24 may have any of a variety of suitable shapes, for example but by no means limited to convex, round convex, ovoid convex, rounded rectangular convex, concave, round concave, ovoid concave and rounded rectangular concave. The base 24 may otherwise be shaped to match the contour of the surface of the body region to be compressed. As a result of these arrangements, different compression may or may not be applied at the center of the base 24 than is applied at the edges. For example, when the base is concave, more pressure is applied at the edges of the base 24 whereas when the base is convex, more pressure is applied at the center of the base 24. The base 24 may be the end of the threaded bolt 20 which contacts the user. In other embodiments which include a threaded bolt assembly, as shown in FIG. 8 and as discussed below, the base 24 is the surface of the pressure foot 60 which contacts the user. As shown in FIG. 3, the top 26 of the threaded bolt 20 includes turning means 28 for adjusting the position of the threaded bolt 20 within the threaded hole 14, as discussed below.

The turning means 28 may comprise any suitable means known in the art for turning a bolt, for example, but by no means limited to a dial, a groove or slot for a coin, a key arrangement wherein a separate key is fitted into a specifically shaped slot, a socket arranged to accept an Allen key, or a D-ring that flips up to a vertical position when in use but lies in a horizontal position when not in use. It is of note that other suitable turning means known in the art may also be used.

Figure 9:
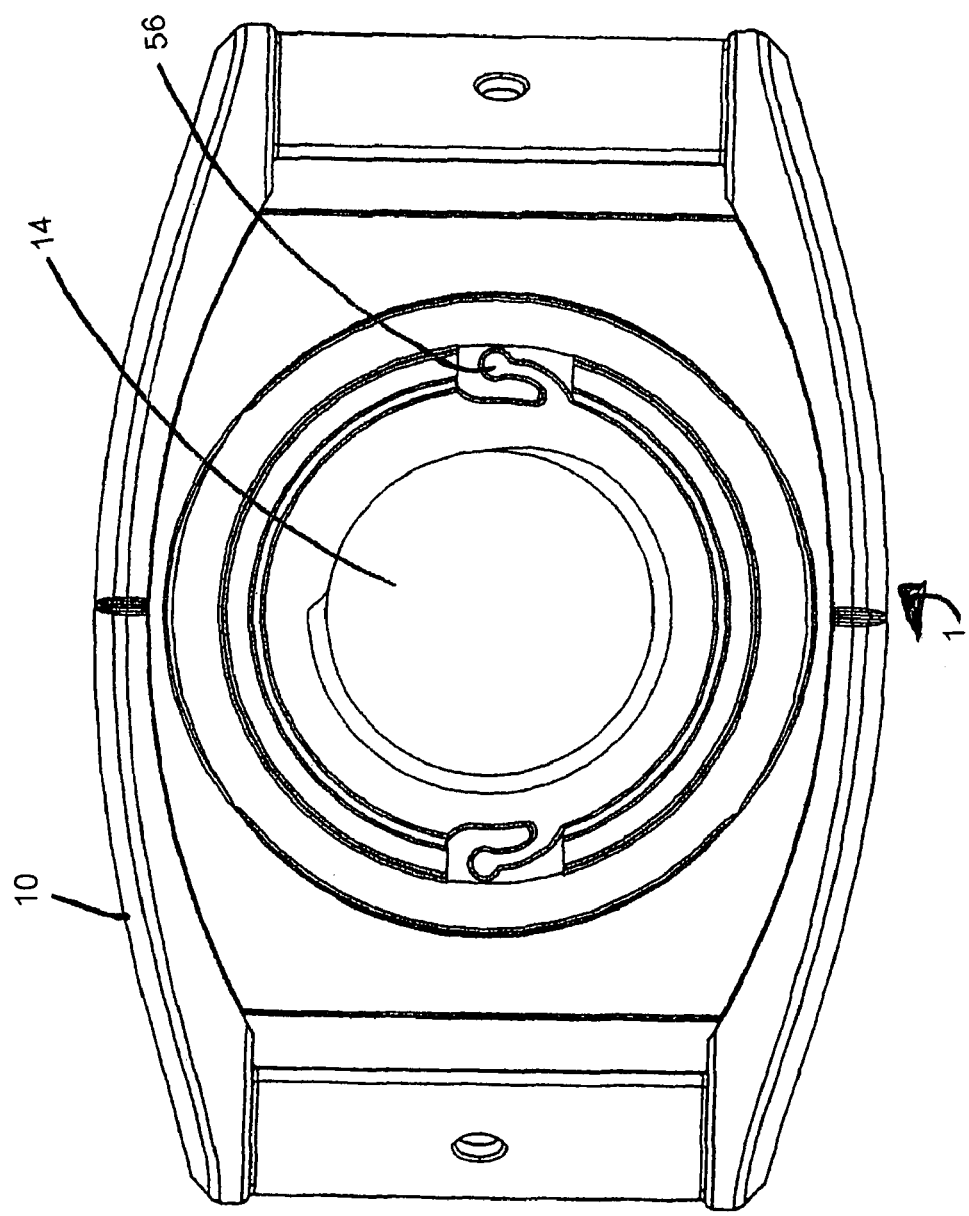
FIG. 9 is a top view of one embodiment of the mounting plate.

In some embodiments, shown for example in FIGS. 8 and 9, the turning means 28 comprises a dial 50 that may include a ratcheting means. The ratcheting means provides the user with a sense of quantifying the compression, such that with each ratchet click, either more or less compression is applied. The pseudo-locking aspect of the ratchet also reduces the tendency for the soft tissues to force the bolt to unscrew—away from the body—as may occur during vigorous muscle contraction. In some embodiments, the inside surfaces of the sides or top of the dial 50 have multiple female indents within which the male mounting plate ratchet buds 56 fall so as to create the ratchet effect as the dial is turned and as the mounting plate (or main body) remains stationary.

In one embodiment, a spring detent assembly may be included on the top of the mounting plate, comprising a spring-loaded ball bearing arranged to ratchet up into respective ones of multiple female indents on the undersurface of the dial 50, in order to achieve a pseudo-locking effect.

Figure 10A:
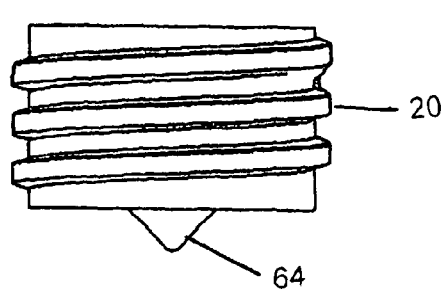
FIG. 10A is a side view of one embodiment of the middle section of the threaded bolt assembly.
Figure 10B:
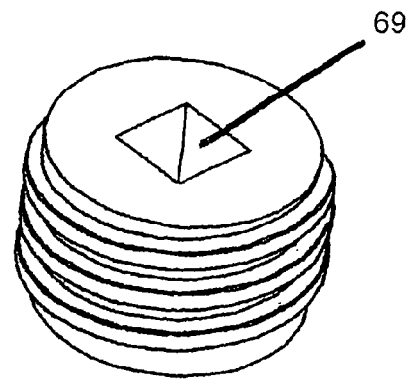
FIG. 10B is a perspective view of one embodiment of the middle section of the threaded bolt assembly.
Figure 11:
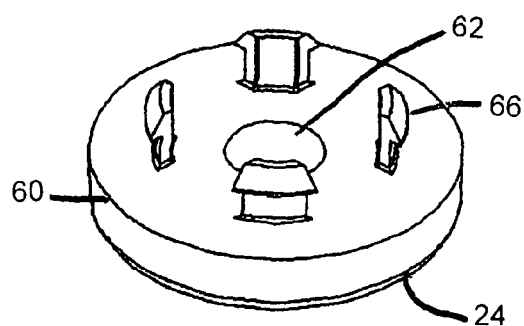
FIG. 11 is a perspective view of one embodiment of the pressure foot.
Figure 12:
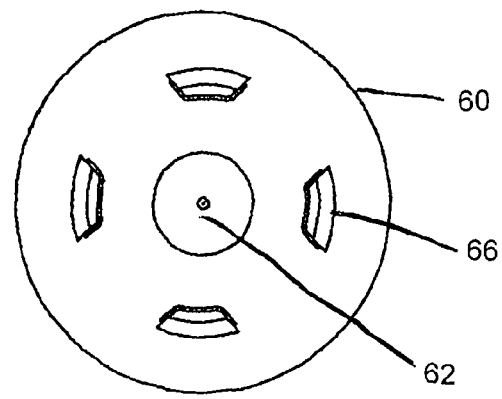
FIG. 12 is a top view of one embodiment of the pressure foot.

In some embodiments, the threaded bolt 20 and the turning means 28 may be replaced by a threaded bolt assembly as shown in FIG. 8. However, as will be appreciated by one of skill in the art, the threaded bolt assembly still comprises a threaded bolt and turning means in addition to a pressure foot, as discussed herein and it is to be understood that the terms threaded bolt and threaded bolt assembly are largely interchangeable as used herein. That is, in many embodiments, a threaded bolt assembly may be substituted for a threaded bolt. In these embodiments, the threaded bolt assembly is comprised of three parts which are mounted within the threaded hole 14 of the mounting plate 10. The three parts from top to bottom are the dial 50, the allen cylinder 20 and the pressure foot 60. As will be appreciated by one of skill in the art, as can be seen from the drawings, the threaded bolt and the allen cylinder attached to the pressure foot are functionally identical and are therefore referred to by the same reference number. However, the term "allen cylinder" is used in the following description for ease of understanding the invention. The dial 50 may in turn, in some embodiments, be held down against the mounting plate 10 by a retainer plate 67. The dial 50 includes a male alien 68 which projects downwards into a female alien 69, as shown in FIG. 10B. As the dial 50 is turned, the resulting rotation is applied to the allen cylinder 20. The rotation of the allen cylinder 20 within the threaded hole 14 results in the alien cylinder moving either up or down in relation to the mounting plate 10 and to the user's tissues. Thus, the simple rotation of the dial 50 is converted to rotation combined with upward or downward movement of the alien cylinder 20. In some embodiments, the pressure foot 60 is snap-fitted into the bottom of the alien cylinder 20 by means of clips 66 (FIGS. 8, 11 and 12). As will be appreciated by one of skill in the art, in these embodiments, the pressure foot 60 is mounted onto the alien cylinder 20 such that turning of the alien cylinder results in little or no turning of the pressure foot 60. For instance, the alien cylinder may include a geometric protrusion 64 at the bottom of the alien cylinder 20 which may be substantially cone-shaped or ball-shaped. The pressure foot 60 in turn may include a geometric opening 62 at the top center aspect of the pressure foot 60 which is shaped to accept the geometric protrusion 64 therein, for example, substantially cone-shaped or bowl-shaped. The resultant "cone in cone" or "ball in bowl" configuration limits the extent to which the rotation of the alien cylinder 20 is conducted to the pressure foot 60. The pressure foot 60 therefore moves up and down in unison with the alien cylinder 20, but with minimal resultant rotation of the pressure foot 60. The advantage of this design is to allow the user to increase or decrease soft tissue compression at the site where the pressure foot 60 contacts the body, with little or no torque or friction applied to the skin surface. In another embodiment, in lieu of using a "cone in cone" or "ball in bowl" configuration, metal and/or plastic bearings may be introduced between the alien cylinder 20 and the pressure foot 60 in order to limit the extent to which the spin of the first part is conducted to the second part. In sum, dial 50 rotation is transferred to and added to alien cylinder 20 upward and downward movement. Allen cylinder 20 upward and downward movement is transferred to the pressure foot 60 substantially in the absence of rotation or spin. The pressure foot 60 compresses tissue with minimal friction applied.

In some embodiments, the turning means 28 may include a locking pin or similar arrangement and the top of the threaded hole 14 may include a plurality of slots for accepting the locking pin therein. As will be appreciated by one of skill in the art, this arrangement enables the turning means 28 to be engaged and to be locked into place on the plate at a specific position. As a result of this arrangement, the turning means 28 may be engaged at a first position such that a given amount of pressure is applied to a tissue portion. At any time, the locking pin may be disengaged and the turning means 28 turned prior to reengaging the locking pin in a different slot such that the pressure applied to the tissue portion is either increased or decreased. In this manner, predictable, reproducible yet differing amounts of pressure may be applied using the device, as discussed below.

As will be appreciated by one of skill in the art, a device as described herein may include a mounting plate 10 and a threaded bolt assembly or threaded bolt 20 in combination with any of the described strap arrangements, any of the described turning means 28, and any of the described base 24 shapes, and any of the pressure foot 60 shapes. It is further of note that the device comprises either a single threaded bolt or a single threaded bolt assembly or two or more threaded bolt assemblies where any of these combinations may either share the same or use separate pressure feet 60. In addition, any of such threaded bolt combinations may be mounted on one or each of two adjacent mounting plates 10.

The device 1 may also include straps or other such connectors known in the art which are inserted into the slots 12 for securing the device 1 onto the user, as discussed below. For example, the straps may include a buckle and a series of holes, attachment material such as Velcro™, buttons and button holes or other such arrangements known in the art. As will be appreciated by one of skill in the art, any suitable strapping arrangement or strapping materials known in the art may be used in combination with the devices described herein. For each compression device proposed herein, in order to encircle the selected body part, there may be 1 or 2 straps connected in series lengthwise to 1 or 2 mounting plates. The strap(s) are of a material that follows the contour of the selected body part. The strap(s) will be either mildly elastic or substantially inelastic relative to the tensile loads which are applied to it in a lengthwise, circumferential direction.

It is of note that as used herein, "user" generally refers to the individual in need of soft tissue compression who may also be referred to as the patient or client. However, in other embodiments, the user may be for example a veterinarian or other individual trained or otherwise knowledgeable in the care of animals who applies the device to an animal. In other embodiments, the user may be an individual with medical or medicinal or therapeutic training who applies the device to a patient or client during the course of treatment. It is noted that the meaning of "user" and "patient" will be clear to one of skill in the art given the context in which these terms are used.

For use, in some embodiments, the threaded bolt 20 is inserted into the threaded hole 14 such that the threaded bolt 20 engages the threaded hole 14. The threaded bolt 20 is then turned using the turning means 28 until the base 24 is at least flush with or extends deep to the base 18 of the mounting plate 10. In some embodiments, the device 1 may be packaged in this manner or the device 1 may be packaged such that the threaded bolt 20 is not inserted into the threaded hole 14.

For use, in some embodiments, the three part threaded bolt assembly consisting of the dial 50, the allen cylinder 20 and the pressure foot 60 is inserted into the threaded hole 14 such that the threaded bolt assembly engages the threaded hole 14. The threaded bolt assembly is then turned using the dial 50 until the pressure foot is at least flush with or extends deep to the base 18 of the mounting plate 10. The device 1 may be packaged in this manner or the device 1 may be packaged such that the threaded bolt assembly or its component parts are not assembled nor inserted into the threaded hole 14.

In use, the user positions the device 1 onto the body part that is in need of soft tissue compression.

Specifically, the device 1 is positioned such that the base 24 of the threaded bolt 20 or the pressure foot 60 of the threaded bolt assembly is aligned over the soft tissues to be compressed. The straps are then tensioned or engaged according to the patient's comfort, thereby securing the device 1 onto the body part of the user. The turning means 28 for example the dial 50 is then used to move the threaded bolt 20 or the threaded bolt assembly down the threaded hole 14 such that the base 24 of the threaded bolt or the pressure foot 60 contacts and compresses the soft tissues. The user continues to turn the turning means 28 until the desired compression has been obtained. Thereafter, the user can use the turning means 28 to increase or decrease compression at any time without the need to disengage the straps or connectors.

Thus, the above-described device is distinguished from the prior art in that many existing devices utilize straps and/or force plates and/or gel pads and/or air-filled pouches wherein compression is adjusted by way of the device's circumferential tensioning mechanism in the absence of a separate means of perpendicular compression adjustment. These devices cannot provide adjustable, perpendicular compression over selected tissues where such forces can be adjusted separately from and in addition to generalized circumferential compression adjustment. The above described device is further distinguished from the prior art in that it utilizes pressure supplied by a threaded bolt or threaded bolt assembly extending through a mounting plate onto soft tissue, specifically, non-spinal and non-boney tissues. The pressure foot can be shaped as mentioned above such that the surface of the pressure foot that articulates with the tissues can be of any suitable shape, for example, the shape to which the condition to be treated is most responsive.

By incorporating a threaded bolt or bolts structure or assembly into a force plate or plates, the user has two distinct and separately-adjustable zones and methods of soft tissue compression: an outer force plate zone which applies more generalized circumferential compression, supplied by the underside or base 18 of the mounting plate 10 and an inner threaded bolt zone which applies more localized and more perpendicular compression via the base 24 or the pressure foot 60.

As discussed above, the base 24 of the threaded bolt 20 or the pressure foot 60 of the threaded bolt assembly which contacts the soft tissues may be convex, which in turn means that central compression from the bolt is greater than peripheral compression from the bolt. Thus, critical tissues located under the center of the base 24 for which greater compression is of greater benefit will receive more compression and adjacent tissues where lesser compression is preferred will receive less compression.

Figure 16:
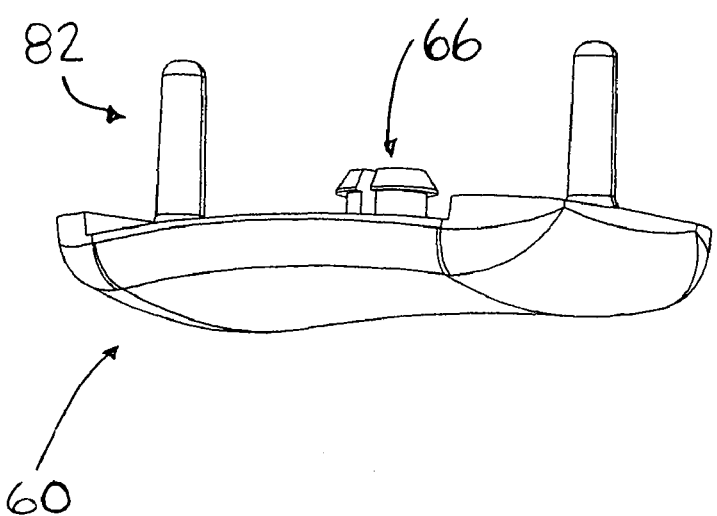
FIG. 16 is a perspective view of an alternative embodiment of the pressure foot.

For example, in an embodiment shown in FIG. 16, the base of the pressure foot 60 has a substantially 'saddle-like' shape. Thus, in these embodiments, the base of the pressure foot 60 is concave in a first direction and convex in a second direction. Specifically, in some uses, the base of the pressure foot 60 is concave in the medial to lateral direction and convex in the proximal to dorsal direction.

In other embodiments, the base 24 of the threaded bolt 20 which contacts the soft tissues is concave, which in turn means that peripheral compression from the bolt is greater than central compression from the articulating surface of the bolt.

In some embodiments of the above-described device where a threaded bolt assembly is used, the device is distinguished from prior art in that the user is able to rotate the adjustment mechanism, for example, the dial 50, with little or no rotation conveyed onto the soft tissues where they are compressed by the pressure foot 60. User comfort is thus enhanced and the potential for damage to the skin surface by friction is thus minimized.

In use, the device 1 operates in some embodiments by turning the dial 50 which in turn causes the threaded bolt 20 or alien cylinder to rotate and move upwards or downwards (depending on the direction of rotation) which in turn causes the pressure foot 60 to move upwards or downwards without rotation.

Figure 15:
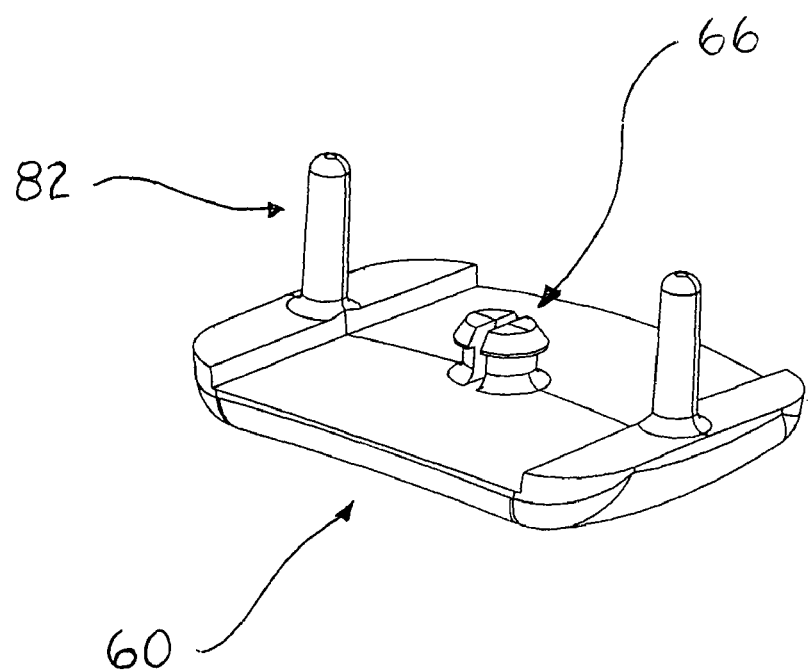
FIG. 15 is a perspective view of an alternative embodiment of the pressure foot.

In an embodiment shown in FIG. 15, the pressure foot 60 further comprises at least one guide post 82. As will be appreciated by one of skill in the art, the guide posts 82 provides further protection against rotation of the pressure foot 60 during use.

As noted above, the device 1 may be used on any area of the body where adjustable, local, perpendicular soft tissue compression is desired for the amelioration, prevention and/or the treatment of, soft tissue symptoms and/or pathology.

Areas, diagnoses and conditions where the device 1 may be applied include and are not limited to the following: Lateral epicondylitis (Tennis Elbow/Lateral elbow pain); Medial epicondylitis (Golfer's Elbow/Medial elbow pain); Carpal tunnel syndrome (CTS); Tendonitis of the wrist extensors musculature (Dorsal wrist and/or dorsal forearm pain); Tendonitis of the wrist flexors musculature (Ventral wrist and/or ventral forearm pain); Nausea; Motion Sickness; Morning Sickness; Patellar tendonitis (Jumper's Knee/Anterior knee pain); Patellofemoral syndrome (PFS); and Chondramalacia patella (CMP). The threaded bolt assembly embodiment may be used to apply acupressure to variously located acupuncture points. The device may also be used by health care professionals for the in-clinic treatment of muscle spasm and trigger points. The device may be used to apply compression to the hind legs of horses for the prevention, control and treatment of problems associated with the suspensory ligament.

Soft tissues which may be compressed using the devices described herein include but are by no means limited to the group consisting of: common extensors forearm muscles compartment; common flexors forearm muscles compartment; P6 or Neiguan acupuncture point on the ventral wrist; patellar tendon; and area overlying the suspensory ligament on a horse hind leg.

It should be noted that the term "Repetitive strain injuries or disorders" (RSI or RSD) may be used to describe orthopaedic conditions whereby repeated and excessive muscular contractions lead to the development of pain, muscle spasm and inflammation. In some cases, the resulting edema applies pressure to and brings about symptoms and/or damage to peripheral nerve tissue. The following aforementioned diagnoses may be classified as Repetitive Strain Injuries: lateral epicondylitis, medial epicondylitis, carpal tunnel syndrome, wrist extensors tendonitis, wrist flexors tendonitis and patellar tendonitis.

For lateral epicondylitis (also referred to as Tennis elbow), which occurs at the proximal forearm, the dorsal plate is positioned as far up the forearm as possible without interfering with elbow flexion and the threaded bolt or threaded bolt assembly is positioned centrally over the extensor compartment forearm musculature brawing a line from the knuckle of the long finger to the lateral epicondyle boney prominence, the threaded bolt is centered or positioned directly over this line so as to allow adjustable compression locally over the central core of the mass of the extensor compartment musculature. An optional ventral plate lies on the opposite side of the upper forearm and the dorsal plate or dorsal and ventral plates are attached to the arm using Velcro™ straps or other strapping means as discussed above, adjustable on the medial and/or the lateral sides. The threaded bolt or threaded bolt assembly allows for adjustable localized pressure over the central core of the extensor compartment musculature based on the user's comfort and based on applying greater compression during periods of increased muscle strain and less compression during periods of decreased muscle strain.

For medial epicondylitis (also referred to as Golfer's elbow), located at the upper forearm or for carpal tunnel syndrome, located at the distal forearm, the ventral plate is positioned as far up the ventral forearm as possible without interfering with elbow flexion, and the threaded bolt or threaded bolt assembly is positioned centrally with respect to the flexor compartment forearm musculature. Drawing a line from the long finger to the medial epicondyle boney prominence, the threaded bolt or threaded bolt assembly is positioned directly over this line so as to allow adjustable compression locally over the central core of the mass of the flexor compartment musculature. An optional mounting plate on the opposite or dorsal side of the upper forearm and the ventral plate or dorsal and ventral plates are attached to the arm using Velcro™ or other strapping means as discussed above, adjustable on the medial and/or the lateral sides. The threaded bolt or threaded bolt assembly allows for adjustable localized pressure over the central core of the flexor compartment musculature based on the user's comfort and based on applying greater compression during periods of increased symptoms or muscle strain or less compression during periods of decreased symptoms or muscle strain.

For carpal tunnel syndrome (including finger or thumb numbness or paresthesia), the device is used as in the case of medial epicondylitis or medial elbow pain. That is, the threaded bolt or threaded bolt assembly is positioned overlying the proximal end of the forearm flexors musculature or compartment. Forearm flexors muscle strain is a contributing factor in the development of carpal tunnel syndrome. Vigorous hand grasping or squeezing and/or repetitive use of the forearm flexors may lead to the development or the exacerbation of carpal tunnel syndrome signs and symptoms. The threaded bolt or threaded bolt assembly is positioned over the center of the proximal forearm flexors muscle group. The user can thus apply a selected compressive force to the muscle tissue via the mounting plate and can apply a different compressive force to the centre of this area of muscle tissue via the threaded bolt assembly pressure foot or the threaded bolt articulating surface. When functional demands on the hand lead to increased forearm strain and potentially to increased exposure to pressure upon the median nerve, the bolt may be adjusted in order that the central bolt compression force exceeds that of the surrounding mounting plate. The ease of compression adjustment afforded by the bolt or bolt assembly facilitates the user's adaptation of compression forces to their comfort, clinical symptoms and functional demands. By restricting muscle belly expansion, the device decreases tensile muscle strain forces within the wrist flexors (palm side) musculature compartment. This in turn decreases the development of ventral forearm tendon swelling, thus limiting pressure on the medial nerve. The mounting plate and threaded bolt or threaded bolt assembly in the case of carpal tunnel syndrome must not be positioned over the distal, ventral forearm area.

As will be appreciated by one of skill in the art, the use of the terms "dorsal", "ventral", "medial", "lateral", "proximal" and "distal", in regard the device components are relative terms and refer to the position of the device relative to the patient in the standard anatomical position and will of course depend on the tissue on which the device is mounted.

For tendonitis of the wrist extensor musculature (dorsal wrist and/or dorsal forearm pain), the mounting plate is located over the dorsal distal forearm and the threaded bolt or threaded bolt assembly within the mounting plate is situated such that threaded bolt compression is between the distal radius and ulna. Side straps and/or an additional optional second ventral force plate complete the circumferential encircling of the distal forearm. Pressure is applied via the threaded bolt as discussed above. Muscle expansion is restricted by the applied compression which, in turn, limits the tensile stresses on muscle fibres and reduces the potential for developing muscle or tendon fibre inflammation.

For tendonitis of the wrist flexor musculature (ventral wrist and/or ventral forearm pain), the mounting plate is located over the ventral (palm side) distal forearm. The threaded bolt or threaded bolt assembly is mounted within the mounting plate and is positioned such that the compression which is applied occurs between the distal radius and ulna. Side straps and/or an additional optional second dorsal mounting plate complete the circumferential encircling of the distal forearm. Muscle expansion is restricted by the applied compression which, in turn, limits the tensile stresses on muscle fibres and reduces the potential for developing muscle or tendon fibre inflammation.

For treatment of nausea, vomiting due to nausea, motion or sea sickness, or morning sickness in pregnancy, the device is positioned on the user's wrist such that the pressure foot 60 of the threaded bolt assembly is over the acupuncture point known in the art as Pericardium 6 or P6 or Neiguan. The P6 point location is between the tendons of the palmaris longus muscle and the flexor carpi radialis muscle, 2 cun acupuncture measuring units proximal to the transverse crease on the ventral aspect of the wrist. The straps are then connected about the user's wrist such that the device is comfortable on the body of the user. The pressure foot 60 is then adjusted using the dial 50 such that acupressure compression is applied to the P6 point in an effort to relieve the applicable symptom. In this arrangement, once the desired compression has been set, there is no need for the user to reach over and apply pressure using his/her opposite hand. The articulating surface of the threaded bolt or of the pressure foot may be contoured to match the shape of the ventral aspect of the forearm region where the P6 point is located.

Figure 17:
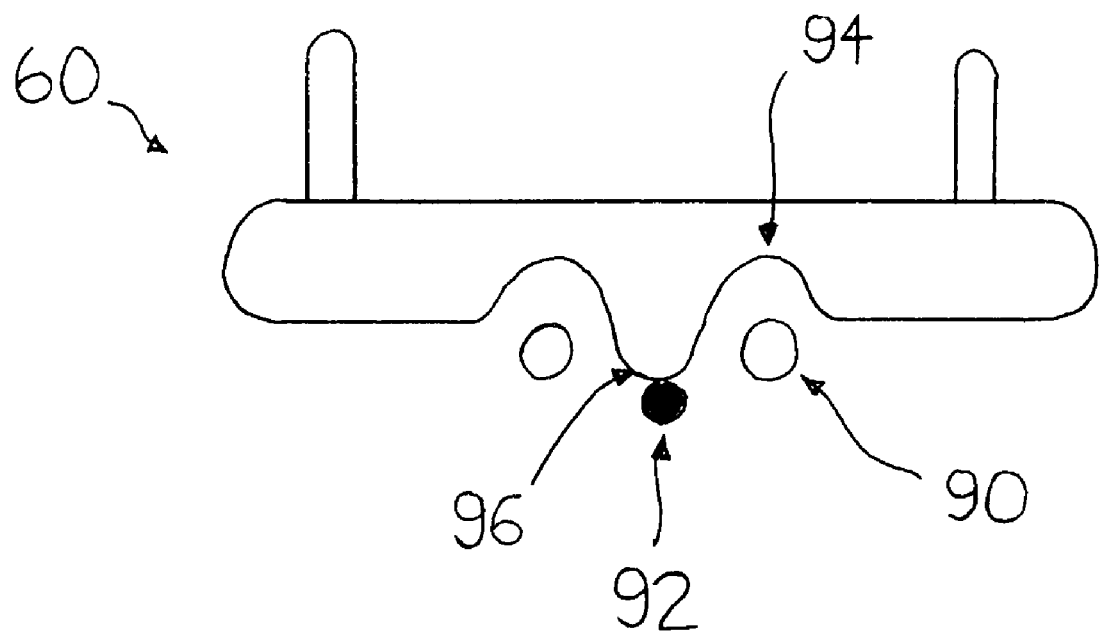
FIG. 17 is a schematic diagram of one embodiment of the pressure foot for use with the P6 point.

In an alternative embodiment of the device 1 shown in FIG. 17, the pressure foot 60 includes two contours 94 and an actuator 96. In use, the device is positioned as generally discussed above and then the contours 94 are arranged such that they are positioned over the tendons 90 of the palmaris longus muscle and the flexor carpi radialis muscle and such that the actuator 96 overlies and indirectly compresses the P6 point 92.

Figure 4:
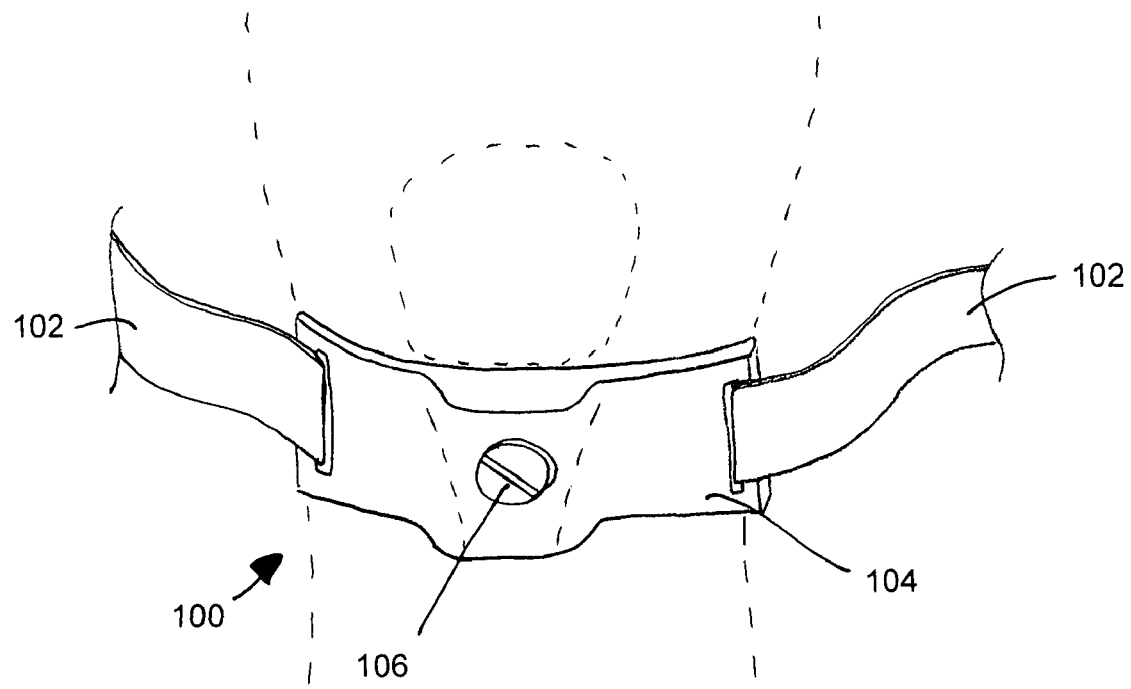
FIG. 4 is a front view of one embodiment of the device.
Figure 5:
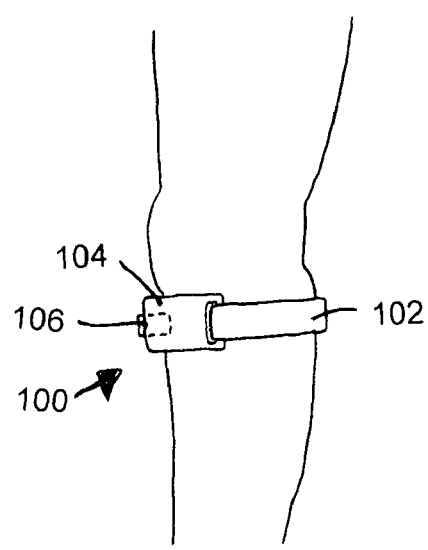
FIG. 5 is a side view of one embodiment of the device in use.

For patellar tendonitis (Jumper's knee), a ventrally-located mounting plate is positioned distal to the lower edge of the patella and follows the contours of the anterior-inferior knee structures with adjustable Velcro™ or other strapping means and posterior padding completing the circumferential coverage of the proximal lower leg. The threaded bolt or threaded bolt assembly is centred directly over the patellar tendon. The bolt allows for adjustable localized pressure over the central core of the patellar tendon based on the user's comfort and based on applying greater compression during periods of increased symptoms and/or patellar tendon strain or lesser compression during periods of decreased symptoms and/or patellar tendon strain. In a preferred embodiment for use on the patellar tendon, the shape of the base is concave, rounded rectangular, although any of the above-mentioned shapes may be utilized. In some embodiments, for example, as shown in FIGS. 4 and 5 for this use, the device 100 comprises a strap 102 arranged to fit around the leg of the patient beneath the kneecap with a mounting plate 104 having a threaded hole and a threaded bolt 106 or threaded bolt assembly as described above. The user can engage the threaded bolt 106 or threaded bolt assembly to apply pressure to the patellar tendon as described and as indicated. It is of note that the embodiments shown in FIGS. 4-7 all include the threaded bolt or threaded bolt assembly described herein. It is further of note that the accompanying figures are for illustrative purposes and that devices having similar features and uses but a very different appearance may also be constructed, as discussed herein.

Figure 6:
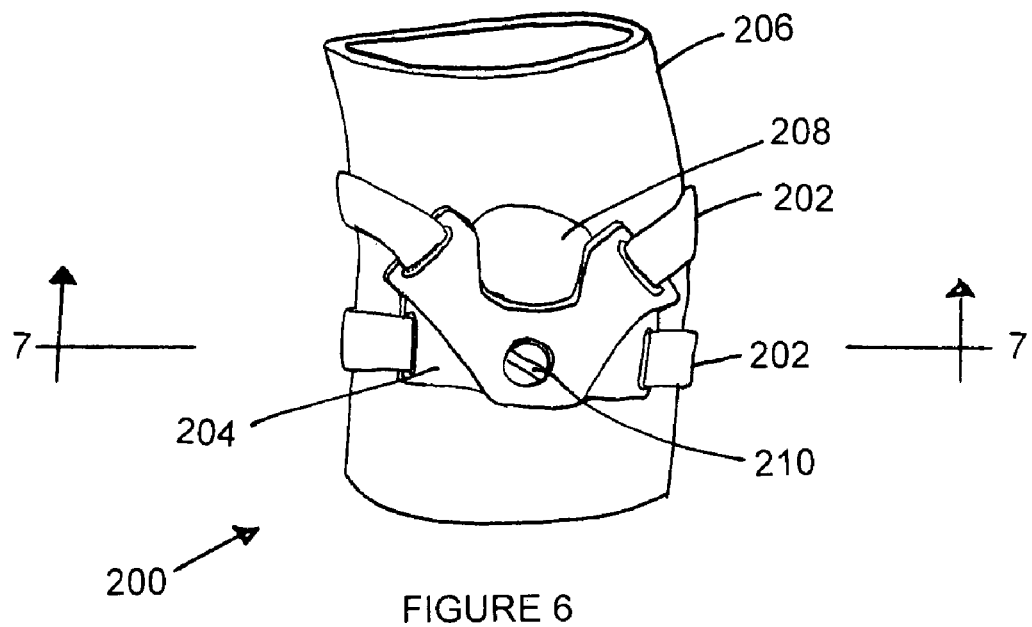
FIG. 6 is a front view of an alternative embodiment of the device.
Figure 7:
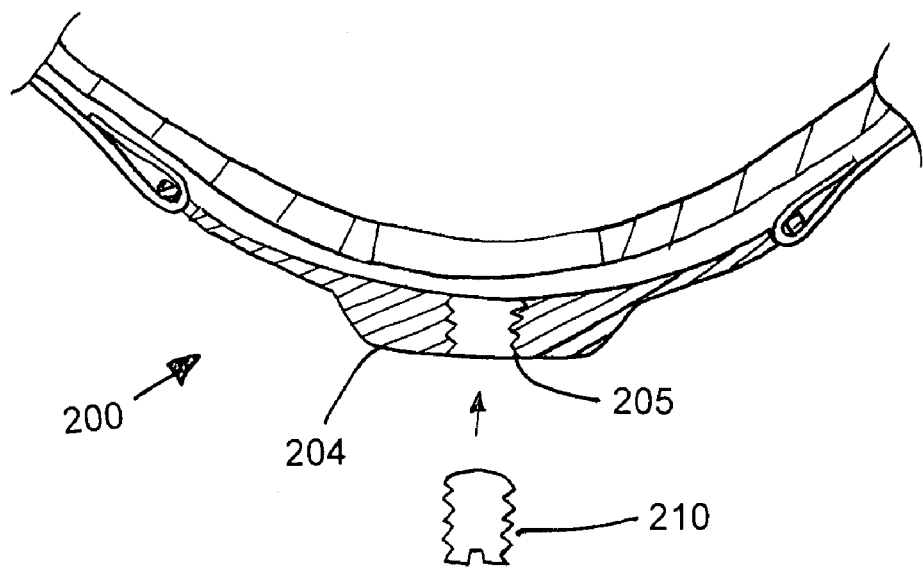
FIG. 7 is a cross-sectional view of the embodiment shown in FIG. 6 along line 7-7.

In other embodiments, shown in FIGS. 6 and 7, the device 200 comprises one or more straps 202 arranged to fit around the leg of the user, a Y-shaped mounting plate 204 having a groove or threaded hole 205, the Y-shaped plate 204 fitting below and on either side of the patella, an optional sleeve 206 that extends above and below the Y-shaped plate 204 and includes a window 208 for the patella and a threaded bolt 210 or threaded bolt assembly arranged for applying pressure to the patellar tendon as described above. The Y-shaped plate 204 provides some medial and/or lateral stability support for the patella around the distal edge and about the medial and lateral edges of the patellar window. For patients with patellar tracking problems—as is common in cases of Patello-Femoral Syndrome (PFS) and Chondromalacia Patella (CMP)—the presence of such medial and lateral support aids in maintaining the patella in a centered position as it moves proximally and distally within the femoral groove.

Any accessible acupressure point as known in the art may be similarly stimulated by positioning a mounting plate over the area of the selected acupuncture point such that the threaded bolt assembly is positioned directly over the point to be compressed. Such a device as described would include the presence of strapping and of strapping connectors as would suit the region of the body where the device is being applied. Acupressure is the stimulation of specific anatomical points by means of soft tissue compression in order to elicit specific responses as may be anticipated by those skilled in the art of acupuncture. Such compression may be applied and adjusted using local perpendicular compression as employed in the instant method.

In another embodiment, there is provided a kit intended solely for rehabilitation or health care professional use which comprises one or more devices as described above, wherein the mounting plates are of differing sizes and shapes and further includes straps of various lengths. Thus, the kit may include: a plurality of straps of varying lengths and/or thicknesses as discussed above; a plurality of mounting plates of different sizes and/or shapes for use on different body regions and for use on individuals of varying sizes; and a plurality of threaded bolts and/or threaded bolt assemblies and/or different shaped bases or pressure feet as described above. As will be appreciated by one of skill in the art, the kit thereby provides suitable components for using the device on several tissue compression sites and on different patients or clients. In these embodiments, the device may be used by a professional to apply pressure to any muscle tissue trigger point (or "knot") within a muscle in spasm in order to deliver staged, progressive ischemic compression to the point with the intent of inducing progressive relaxation of local muscle fibres. This can be achieved using the threaded bolt 20 or threaded bolt assembly as described above.

Figure 13:
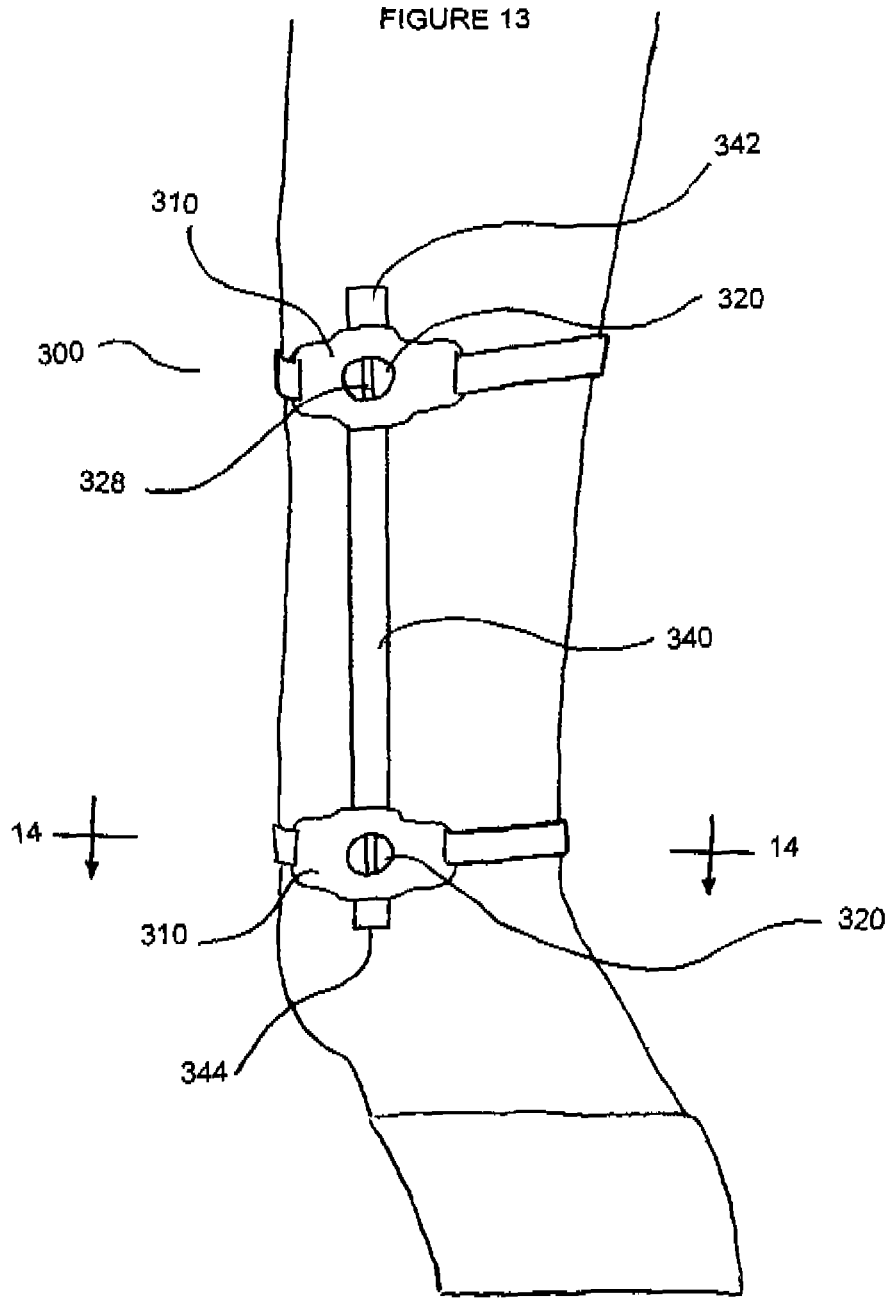
FIG. 13 is a side view of an embodiment of the device arranged for use in the region of the suspensory ligament of a horse.
Figure 14:
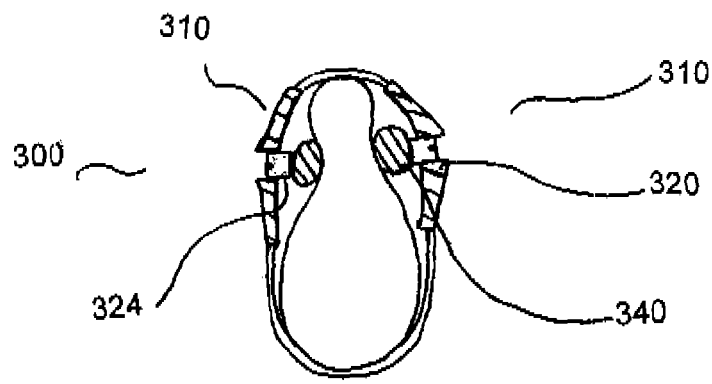
FIG. 14 is a cross-sectional view of the embodiment shown in FIG. 13 along line 14-14.

In other embodiments, the current invention may be used for a variety of veterinary purposes including but not limited to the application of compression to the hind legs of horses in the region of the suspensory ligament. One example of such a device is shown in FIGS. 13 and 14. Shown therein is an embodiment of the device 300 which comprises either two or four mounting plates 310 (one on each side or two on each side) and four threaded bolt assemblies 320 devices arranged generally as illustrated (at least two on each side). The elongate pressure foot or bar 340 on this device would apply compression to each side of the horse's hind leg, specifically such that there is one bar 340 on either side of the suspensory ligament (FIG. 14). Each foot or bar 340 derives compression from at least one mounting plate 310, where each plate houses at least one threaded bolt assembly 320. The bolt assembly 320 presses upon one end of the bar 340 when engaged, by this means allowing the user to control compression along the length of the bar 340 from either side of the leg. The mounting plates 310 on either side of the leg and at the proximal end of the device are then interconnected by straps as are the mounting plates 310 on either side of the leg at the distal end of the device. Specifically, as discussed above, the turning means 328 may be a dial, a screw or any other mechanism described herein. As will be appreciated by one of skill in the art, each threaded bolt assembly may be adjusted individually thereby allowing for a variety of pressures to be applied indirectly to the suspensory ligament. In the practice of veterinary medicine, applying compression over and on either side of the suspensory ligament is recognized as a means of control and of treatment of suspensory ligament problems in horses. The current method of applying compression ensures that more effective compression will be applied to the floor of the groove overlying the suspensory ligament (FIG. 14). It is of note that in another embodiment, the device 300 may be arranged such that one mounting plate is included on each side with a turning means and an alien cylinder at each end of the mounting plate such that the two alien cylinders share a common elongate pressure foot or bar 340. In another embodiment, the mounting plates and threaded bolt assembly parts housed therein may be designed so as to be free to slide up or down the horse's hind leg in order to better control the location of the applied compression.

For safety, at any time that pain or numbness or tingling or hand cyanosis or dizziness or syncope is experienced by the user, the user must do one or more of the following as required in order to eliminate any and all such signs or symptoms:

1) Loosen the circumferential pressure or tension attachments,

2) Withdraw or turn back the threaded bolt or threaded bolt assembly,

3) Remove the entire device.

The device should not be used in the case of any or all of the following:

A) During sleep or when consciousness is not adequate to allow the user to monitor symptomatic responses;

B) In the presence of sensory deficits which may prevent the user from adequately monitoring symptomatic responses;

C) In the presence of circulatory compromise;

D) Over open wounds, burns or frost-bite;

E) In the presence of local skin hypersensitivity or dermatological conditions.

F) To compress directly over a peripheral nerve lesion, for example, over the ulnar nerve in ulnar neuritis or over the distal portion of the median nerve in carpal tunnel syndrome.

In some embodiments, the threaded bolt has a diameter between 5/8" and 1 and 1/2". The threaded hole may have a height allowance of 1/2", and no >1" and no <1/8". As discussed above, the threaded hole 14 has dimensions such that the threaded bolt 20 is securely accepted therein. The diameter allowance for female opening plus side walls to the female opening=no <the diameter of the threaded bolt+1/64" and is no <4/64" and no >1 and 5/8". The pressure foot 60 of the threaded bolt assembly or the base 24 of the threaded bolt shall have dimensions as follows:

a) to apply to the proximal forearm ventral or dorsal compartments=an area of between 3 and 9 cm².

b) to apply to the distal forearm ventral or dorsal compartments or to the P6 acupuncture point=an area of between 1.5 and 5 cm².

c) to apply to the patellar tendon=an area between 4 and 11 cm².

d) to be used in the health care professional kit=various sizes of pressure foot which may be interchangeable.

e) to be used on horse legs=between 2" and 12" in length and between 3/8" and 1 and 1/2" in width.

As will be appreciated by one of skill in the art, these dimensions are for illustrative purposes only and as discussed above any suitable dimensions may be utilized. Specifically, different bolt and plate sizes and shapes may be used within the scope of the invention for a variety of purposes, as discussed above.

In some embodiments, the device may include a timer or a timer may be clipped on to the device 1 for monitoring treatment times.

In yet other embodiments, the straps may be rubber or may be washable. In other embodiments, the straps may include Velcro™ lining and/or may have changeable, replaceable or adjustable straps for use on different body areas and body sizes.

While the preferred embodiments of the invention have been described above, it will be recognized and understood that various modifications may be made therein, and the appended claims are intended to cover all such modifications which may fall within the spirit and scope of the invention.

The invention claimed is:

1. A medical device comprising:
   a mounting plate having a threaded hole extending therethrough, said mounting plate arranged to approximately fit or contour the curvature of a forearm of a user and apply perpendicular compression to said forearm;
   a strap for securing the device onto the forearm of the user and applying circumferential compression to said forearm; and
   a threaded bolt assembly comprising:
      a cylinder arranged for up and down rotation within the threaded hole;
      a pressure foot mounted to the cylinder, said pressure foot for contacting the forearm of the user and providing adjustable perpendicular compression to soft tissues within the forearm, wherein the pressure foot moves up and down with the cylinder; and
      a turning means that causes rotation, the rotation being converted to rotation combined with upward or downward movement of the cylinder within the threaded hole and said upward or downward movement being transferred to the pressure foot substantially in the absence of rotation of the pressure foot.

2. The device according to claim 1 wherein the turning means is a dial.

3. The medical device according to claim 1 wherein the mounting plate includes padding mounted on an underside thereof.

4. A method of supplying perpendicular compression to forearm muscles comprising:
   providing a medical device comprising:
   a mounting plate having a threaded hole extending therethrough, said mounting plate arranged to be fitted over the forearm of a user in need of perpendicular compression to forearm muscles of said user so as to approximately fit the curvature of the forearm to be compressed and apply perpendicular compression to said forearm;
   a strap for securing the device onto the forearm of the user and apply circumferential compression to said forearm; and
   a threaded bolt assembly comprising:
      a cylinder arranged for up and down rotation within the threaded hole;
      a pressure foot mounted to the cylinder, said pressure foot for contacting the forearm of the user and providing adjustable perpendicular compression to soft tissues within the forearm, wherein the pressure foot moves up and down with the cylinder; and
      a turning means that causes rotation, the rotation being converted to rotation combined with upward or downward movement of the cylinder and said upward or downward movement being transferred to the pressure foot substantially in the absence of rotation of the pressure foot;
   positioning the device on the forearm of the user such that the mounting plate fits the curvature of the forearm and the threaded hole lies over the forearm muscles to be compressed;
   applying circumferential compression to the forearm by engaging the strap so that the device is secured on the user's forearm; and
   using the turning means to direct the cylinder down such that the pressure foot contacts the forearm muscles and compresses the forearm muscles until the desired perpendicular compression of the forearm muscles is attained.

5. The method according to claim 4 wherein the mounting plate includes padding mounted on an underside thereof.

6. A method of treating lateral epicondylitis comprising:
   providing a medical device comprising:
      a mounting plate having a threaded hole extending therethrough, said mounting plate arranged to approximately fit or contour the curvature of a forearm of a user in need of treatment for lateral epicondylitis, said mounting plate for applying perpendicular compression to said forearm;
      a strap for securing the device onto the forearm of the user and applying circumferential compression to said forearm; and
      a threaded bolt assembly comprising:
         a cylinder arranged for up and down rotation within the threaded hole;
         a pressure foot mounted to the cylinder, said pressure foot for contacting the forearm of the user and providing adjustable perpendicular compression to soft tissues within the forearm, wherein the pressure foot moves up and down with the cylinder; and
         a turning means that causes rotation, the rotation being converted to rotation combined with upward or downward movement of the cylinder within the threaded hole and said upward or downward movement being transferred to the pressure foot substantially in the absence of rotation of the pressure foot;
   positioning the mounting plate onto the forearm of the user such that the pressure foot is positioned over the mass of the extensor compartment musculature;
   applying circumferential compression to the forearm by engaging the strap so that the device is secured on the user's forearm; and
   turning the turning means to apply perpendicular compression to the central core of the mass of the extensor compartment forearm musculature by contacting the mass of the extensor compartment forearm musculature with the pressure foot, thereby providing perpendicular and circumferential compression during muscle strain.

7. The method according to claim 6 wherein the mounting plate includes padding mounted on an underside thereof.

8. A method of treating medial epicondylitis comprising:
   providing a medical device comprising:
      a mounting plate having a threaded hole extending therethrough, said mounting plate arranged to approximately fit or contour the curvature of a forearm of a user in need of treatment for medial epicondylitis, said mounting plate applying perpendicular compression to said forearm;
      a strap for securing the device onto the forearm of the user and applying circumferential compression to the forearm; and
      a threaded bolt assembly comprising:
         a cylinder arranged for up and down rotation within the threaded hole;
         a pressure foot mounted to the cylinder, said pressure foot for contacting the forearm of the user and providing adjustable perpendicular compression to soft tissues within the forearm, wherein the pressure foot moves up and down with the cylinder; and a turning means that causes rotation, the rotation being converted to rotation combined with upward or downward movement of the cylinder within the threaded hole and said upward or downward movement being transferred to the pressure foot substantially in the absence of rotation of the pressure foot;

positioning the mounting plate on the forearm of the user such that the pressure foot is positioned over the mass of the flexor compartment musculature;

applying circumferential compression to the forearm by engaging the strap so that the device is secured on the user's forearm; and turning the turning means to apply perpendicular compression to the mass of the flexor compartment forearm musculature by contacting the mass of the flexor compartment forearm musculature with the pressure foot, thereby providing perpendicular and circumferential compression during muscle strain.

9. The method according to claim 8 wherein the mounting plate includes padding mounted on an underside thereof.

10. A method of applying acupressure to the pericardium 6 (P6) pressure point comprising:

providing a medical device comprising:

a mounting plate having a threaded hole extending therethrough, said mounting plate arranged to be fitted over a wrist of a user in need of acupressure to the P6 pressure point, said mounting plate applying perpendicular compression to said wrist;

a strap for connecting the device about the wrist and applying circumferential compression to said wrist;

a threaded bolt assembly comprising:

a cylinder arranged for up and down rotation within the threaded hole;

a pressure foot mounted to the cylinder, said pressure foot for contacting the P6 pressure point of said user and providing adjustable perpendicular compression to the P6 pressure point, wherein the pressure foot moves up and down with the cylinder; and a turning means that causes rotation, the rotation being converted to rotation combined with upward or downward movement of the cylinder within the threaded hole and said upward or downward movement being transferred to the pressure foot substantially in the absence of rotation of the pressure foot;

positioning the mounting plate on the wrist of the user suffering from nausea, motion sickness, sea sickness, or morning sickness in pregnancy such that the threaded bolt is over the P6 pressure point wherein the P6 pressure point is located between the tendons of the palmaris longus muscle and the flexor carpi radialis muscle of the user;

engaging the strap so that the device is connected about the user's wrist; and compressing the P6 pressure point between the tendons of the palmaris longus muscle and the flexor carpi radialis muscle by turning the turning means such that the threaded bolt compresses the P6 pressure point.

11. The method according to claim 10 wherein the mounting plate includes padding mounted on an underside thereof.

12. A method of treating patellar tendonitis comprising:

providing a medical device comprising:

a mounting plate having a threaded hole extending therethrough, said mounting plate overlying the patellar tendon at the anterior-inferior knee of a user in need of treatment for patellar tendonitis, said mounting plate for applying perpendicular compression to said knee;

a strap for attaching the device around the user's knee and applying circumferential compression to said knee;

a threaded bolt assembly comprising:

a cylinder arranged for up and down rotation within the threaded hole;

a pressure foot mounted to the cylinder, said pressure foot for contacting the P6 pressure point of said user and providing adjustable perpendicular compression to the P6 pressure point, wherein the pressure foot moves up and down with the cylinder; and a turning means that causes rotation, the rotation being converted to rotation combined with upward or downward movement of the cylinder within the threaded hole and said upward or downward movement being transferred to the pressure foot substantially in the absence of rotation of the pressure foot;

positioning the mounting plate onto the contours of the anterior-inferior knee structures such that the threaded bolt is over the patellar tendon of the user;

applying general circumferential pressure to the leg by engaging the strap and securing the device to the leg of the user; and compressing the patellar tendon by turning the turning means so that the threaded bolt applies perpendicular compression to the patellar tendon, thereby treating patellar tendonitis.

13. The method according to claim 12 wherein the mounting plate includes padding mounted on an underside thereof.

* * * * *

UNITED STATES PATENT AND TRADEMARK OFFICE
CERTIFICATE OF CORRECTION

| | | |
|---|---|---|
| PATENT NO. | : 7,780,612 B2 | |
| APPLICATION NO. | : 11/702123 | |
| DATED | : August 24, 2010 | |
| INVENTOR(S) | : Bradley Allan Ross | |

Figure 2:
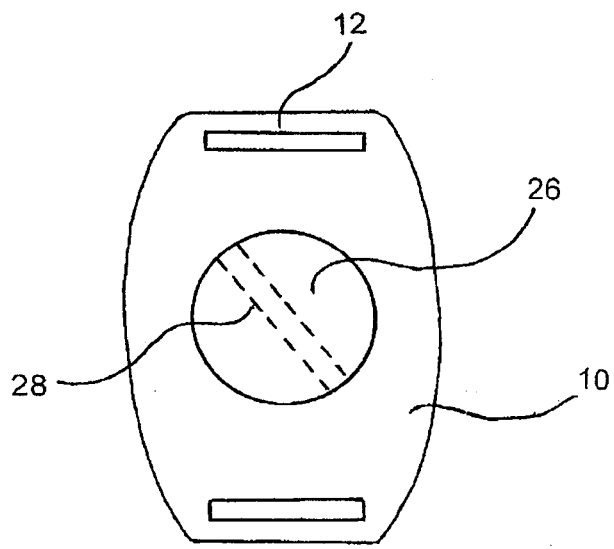
FIG. 2 is a top view of one embodiment of the mounting plate and adjusting means of the device.

It is certified that error appears in the above-identified patent and that said Letters Patent is hereby corrected as shown below:

In the drawings delete Figures 1, 2 and 3 and insert the following Figures 1, 2 and 3.

Signed and Sealed this
Twenty-ninth Day of May, 2012

David J. Kappos
*Director of the United States Patent and Trademark Office*